US 6,600,051 B2

(12) United States Patent
Tully

(10) Patent No.: US 6,600,051 B2
(45) Date of Patent: Jul. 29, 2003

(54) FACTORY SCALE PROCESS FOR PRODUCING CRYSTALLINE ATORVASTATIN TRIHYDRATE HEMI CALCIUM SALT

(75) Inventor: William Tully, Midleton (IE)

(73) Assignee: Warner-Lambert Company, Morris Plains, NJ (US)

(*) Notice: Subject to any disclaimer, the term of this patent is extended or adjusted under 35 U.S.C. 154(b) by 38 days.

(21) Appl. No.: 10/172,051

(22) Filed: Jun. 14, 2002

(65) Prior Publication Data

US 2002/0156294 A1 Oct. 24, 2002

Related U.S. Application Data

(63) Continuation of application No. PCT/IE00/00150, filed on Dec. 18, 2000.

(30) Foreign Application Priority Data

Dec. 17, 1999 (IE) .............................................. 00132/99

(51) Int. Cl.⁷ ......................................... C07D 207/327
(52) U.S. Cl. ....................................................... 548/537
(58) Field of Search ......................................... 548/537

(56) References Cited

U.S. PATENT DOCUMENTS

| | | | |
|---|---|---|---|
| 4,681,893 A | 7/1987 | Roth | 514/422 |
| 5,003,080 A | 3/1991 | Butler et al. | 548/517 |
| 5,097,045 A | 3/1992 | Butler et al. | 549/373 |
| 5,103,024 A | 4/1992 | Millar et al. | 549/373 |
| 5,124,482 A | 6/1992 | Butler et al. | 564/169 |
| 5,149,837 A | 9/1992 | Butler et al. | 549/333 |
| 5,155,251 A | 10/1992 | Butler et al. | 558/442 |
| 5,216,174 A | 6/1993 | Butler et al. | 548/517 |
| 5,245,047 A | 9/1993 | Butler et al. | 548/517 |
| 5,248,793 A | 9/1993 | Millar et al. | 549/375 |
| 5,273,995 A | 12/1993 | Roth | 514/422 |
| 5,280,126 A | 1/1994 | Butler et al. | 548/517 |
| 5,298,627 A | 3/1994 | Butler et al. | 548/517 |
| 5,342,952 A | 8/1994 | Butler et al. | 546/245 |
| 5,397,792 A | 3/1995 | Butler et al. | 514/326 |
| 5,446,054 A | 8/1995 | Butler et al. | 514/326 |
| 5,470,981 A | 11/1995 | Butler et al. | 546/207 |
| 5,489,690 A | 2/1996 | Butler et al. | 546/245 |
| 5,489,691 A | 2/1996 | Butler et al. | 548/517 |
| 5,510,488 A | 4/1996 | Butler et al. | 546/207 |
| 5,969,156 A | 10/1999 | Briggs et al. | 548/537 |
| 5,998,633 A | 12/1999 | Jacks et al. | 549/313 |
| 6,087,511 A * | 7/2000 | Lin et al. | |

FOREIGN PATENT DOCUMENTS

| | | |
|---|---|---|
| WO | 9703958 | 2/1997 |
| WO | 9932434 | 7/1999 |

OTHER PUBLICATIONS

PCT International Search Report, PCT/IE00/00150 (2000).
Brower et al., "The Synthesis of (4R–cis)–1,1–Dimethylethyl 6–cyanomethyl–2,2–dimethyl–1,3–dioxane–4–acetate, a Key Intermediate for the Preparation of CI–981, a Highly Potent, Tissue Selective Inhibitor of HMG–CoA Reductase", *Tetrahedron Letters*, vol. 33, No. 17, 1992, pp. 2279–2282.
Baumann et al., "The Convergent Synthesis of CI–981, an Optically Active, Highly Potent, Tissue Selective Inhibitor of HMG–CoA Reductase", *Tetrahedron Letters*, vol. 33, No. 17, 1992, pp. 2283–2284.

* cited by examiner

*Primary Examiner*—Joseph K. McKane
*Assistant Examiner*—Sonya Wright
(74) *Attorney, Agent, or Firm*—Francis J. Tinney

(57) ABSTRACT

A factory scale process for producing crystalline atorvastatine trihydrate hemi calcium salt includes the addition of extra methyl tert-butyl ether to the reaction mixture to supersaturate the crystallization matrix. A seed slurry is made up in a make-up/delivery vessel and delivered, under pressure, to the reaction mixture. The process produces crystalline atorvastatin calcium within a consistent size range on a factory scale.

7 Claims, 3 Drawing Sheets

FACTORY SCALE PROCESS FOR PRODUCING CRYSTALLINE ATORVASTATIN TRIHYDRATE HEMI CALCIUM SALT

RELATED APPLICATIONS

This application is a continuation of International Application PCT/IE 00/00150 filed Dec. 18, 2000, which claims priority from International Application PCT/IE 99/00132 filed Dec. 17, 1999 all of which are incorporated herein by reference in their entirety.

FIELD OF THE INVENTION

The invention relates to an improved process for producing crystalline atorvastatin calcium which is known by the chemical name [R-(R*,R*)]-2-(4-fluorophenyl)-$\beta$,$\delta$-dihydroxy-5-(1-methylethyl)-3-phenyl-4-[(phenylamino) carbonyl]-1H-pyrrole-1-heptanoic acid hemi calcium salt.

BACKGROUND OF THE INVENTION

Atorvastatin is useful as a selective and competitive inhibitor of the enzyme 3-hydroxy-3-methylglutaryl-coenzyme A (HMG-CoA) reductase, the rate-limiting enzyme that converts 3-hydroxy-3-methylglutaryl-coenzyme A to mevalonate, a precursor of sterols such as cholesterol. The conversion of HMG-CoA to mevalonate is an early and rate-limiting step in cholesterol biosynthesis.

Atorvastatin as well as some of its metabolites are pharmacologically active in humans and are thus useful as a hypolipidemic and hypocholesterolemic agent. The liver is the primary site of action and the principal site of cholesterol synthesis. Clinical and pathological studies show that elevated plasma levels of total cholesterol and associated triglycerides promote human atherosclerosis and are risk factors for developing cardiovascular disease.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N, 4-diphenyl-1-[(2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N, 4-diphenyl-1-[(2-tetrahydro-4-hydroxy-6-oxo-2H-pyran-2-yl)ethyl]-1H-pyrrole-3-carboxamide, i.e., [R-(R*,R*)]-2-(4-fluorophenyl)-$\gamma$, $\delta$-dihydroxy-5-(1-methylethyl)-3-enyl-4-[(phenylamino)carbonyl]-1H-pyrrole-1-heptanoic acid.

The above described atorvastatin compounds have been prepared by a superior convergent route disclosed in the following U.S. Pat. Nos. 5,003,080; 5,097,045; 5,103,024; 5,124,482; and 5,149,837 which are herein incorporated by reference and Baumann K. L., Butler D. E., Deering C. F., et al, *Tetrahedron Letters* 1992;33:2283–2284.

One of the critical intermediates disclosed in U.S. Pat. No. 5,097,045 has also been produced using novel chemistry, as disclosed in U.S. Pat. No. 5,155,251 which is herein incorporated by reference and Brower P. L., Butler D. E., Deering C. F., et al, *Tetrahedron Letters* 1992;33:2279–2282.

U.S. Pat. Nos. 5,216,174; 5,245,047; 5,248,793; 5,280, 126; 5,397,792; 5,342,952; 5,298,627; 5,446,054; 5,470, 981; 5,489,690; 5,489,691; 5,109,488; 5,969,156; U.S. Pat. No. 6,087,511; U.S. Pat. No. 5,998,663 and WO99/32434 which are herein incorporated by reference, disclose various processes and key intermediates for preparing atorvastatin.

Atorvastatin is prepared as its calcium salt, i.e., [R-(R*, R*)]-2-(4-fluorophenyl)-$\gamma$, $\delta$-dihydroxy-5-(1-methylethyl)-3-phenyl-4-[(phenylamino)carbonyl]-1H-pyrrole-1-heptanoic acid calcium salt (2:1). The calcium salt is desirable since it enables atorvastatin to be conveniently formulated in, for example, tablets, capsules, lozenges, powders, and the like for oral administration.

It was unexpectedly found that on scale-up to a commercial factory scale, the average crystal size of atorvastatin calcium was in some instances smaller than expected.

The object of the present invention is therefore to provide a process for producing crystalline atorvastatin calcium on a factory scale which routinely and consistently produces material in a consistent size range.

SUMMARY OF THE INVENTION

According to the invention there is provided a factory scale process for producing crystalline atorvastatin trihydrate hemi calcium salt comprising the steps of:

(a) reacting a mixture of atorvastatin lactone, methanol, and methyl tert-butyl ether with sodium hydroxide to form the ring-opened sodium salt;

(b) forming a product rich aqueous layer and an organic layer comprising methyl tert-butyl ether containing impurities;

(c) removing the organic layer comprising methyl tert-butyl ether containing impurities;

(d) extracting the product rich aqueous layer with methyl tert-butyl ether;

(e) adding an extra charge of methyl tert-butyl ether to a vessel containing the product rich aqueous layer in an amount of at least 1% w/v of the contents of the vessel;

(f) sealing the reaction vessel;

(g) heating the contents of the sealed reaction vessel to 47° C. to 57° C. in the presence of the extra charge of methyl tert-butyl ether which saturates the the crystallization matrix on heating; and (h) adding calcium acetate hemihydrate to the sealed reaction vessel to form atorvastatin trihydrate hemi calcium salt.

It was found that the addition of an extra charge of methyl tert-butyl ether after extractions with methyl tert-butyl ether ensures a saturated crystallzation matrix at the elevated temperature which has sufficient organic solvent content compensating for any increased solubility with heat and any loss to the headspace, and was surprisingly found to result in the formation of crystals of atorvastatin calcium within a consistent size range on a factory scale.

In a preferred embodiment of the invention the process includes the steps of:

preparing a mixed slurry in a pressurized slurry make-up/delivery vessel by:
(a) introducing water into the make-up/delivery vessel;
(b) introducing methanol into the make-up/delivery vessel;
(c) subsequently adding seed crystals of atorvastatin trihydrate hemi calcium salt to the make-up/delivery vessel; and
(d) after addition of calcium acetate hemihydrate to the vessel, adding the seed mixture thus formed from the pressurized make-up/delivery vessel to the sealed reaction vessel under pressure to maintain saturation of the crystallization matrix by methyl tert-butyl ether at the elevated temperature in the reaction vessel.

Preferably, the process includes the step of agitating the methanol and water in the make-up/delivery vessel to produce a solvent mixture before addition of the seed crystals to the make-up/delivery vessel.

In one embodiment of the invention the process includes the step of mixing the mixture of water, methanol, and seed crystals of atorvastatin trihydrate hemi calcium salt in the make-up/delivery vessel to form a seed crystal slurry for delivery from the pressurised slurry make-up/delivery vessel into the sealed pressurized reaction vessel containing the heated crystallization matrix saturated with methyl tert-butyl ether.

In a preferred embodiment the make-up/delivery vessel is pivotally mounted on a support frame and the methanol and water mixture are agitated by rocking the make-up/delivery vessel to produce the solvent mixture.

In a particularly preferred embodiment the make-up/delivery vessel is pivotally mounted on a support frame, and the solvent mixture and seed crystals are mixed by rocking the make-up/delivery vessel to form the seed crystal slurry.

The invention also provides a process which allows a seed slurry of atorvastatin to be prepared quickly and efficiently, and which can be introduced to the reaction vessel under pressure thereby maintaining a sealed system. A sealed system is maintained throughout the atorvastatin calcium crystallization process to prevent the loss of solvents to evaporation.

In one embodiment of the invention delivery of the seed slurry from the pressurised make-up/delivery vessel into the sealed pressurized reaction vessel is commenced not more than 5 minutes after commencement of the addition of calcium acetate.

BRIEF DESCRIPTION OF THE INVENTION

The invention will be more clearly understood from the following description given by way of example only with reference to the accompanying drawings in which.

DETAILED DESCRIPTION OF THE INVENTION

The invention will be more clearly understood from the following description given by way of example only.

Crystalline atorvastatin calcium is a white to off-white solid that is insoluble in aqueous solutions of pH 4 and above. Atorvastatin calcium is very slightly soluble in distilled water, pH 7.4 phosphate buffer and acetonitrile, slightly soluble in ethanol and freely soluble in methanol. Crystalline atorvastatin calcium trihydrate has the following chemical structure:

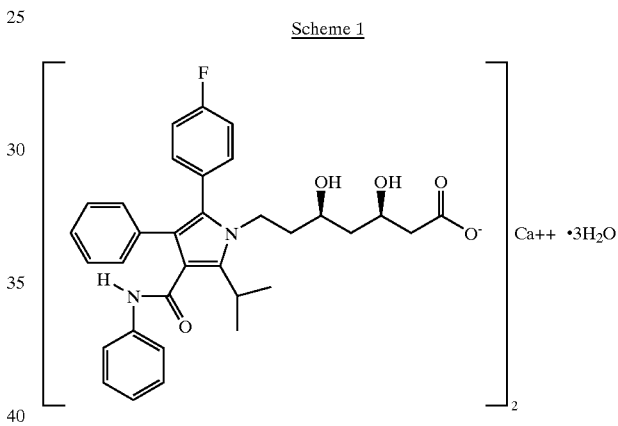

Scheme 1

The process for the preparation of atorvastatin calcium from atorvastatin lactone involves saponification in a water/methyl alcohol/methyl tert-butyl ether (2-methoxy-2-methyl-propane; tert-butyl methyl ether) mixture with sodium hydroxide. The aqueous layer containing the sodium salt of atorvastatin is washed with methyl tert-butyl ether to remove small quantities of process impurities. A small aliquot of methyl tert-butyl ether is added to the crystallization matrix. Sodium-to-calcium salt metathesis with concurrent crystallization is accomplished by the slow addition of an aqueous calcium acetate solution to the sodium salt solution. To ensure crystallization simultaneous with addition, the reaction mixture is seeded with crystalline atorvastatin shortly after the start of the calcium acetate addition. The product is isolated by filtration and, after washing with water/methyl alcohol and water, is centrifuged, vacuum dried, and milled to give crystalline atorvastatin as the trihydrate. This reaction scheme is shown in Scheme 2 below.

Scheme 2

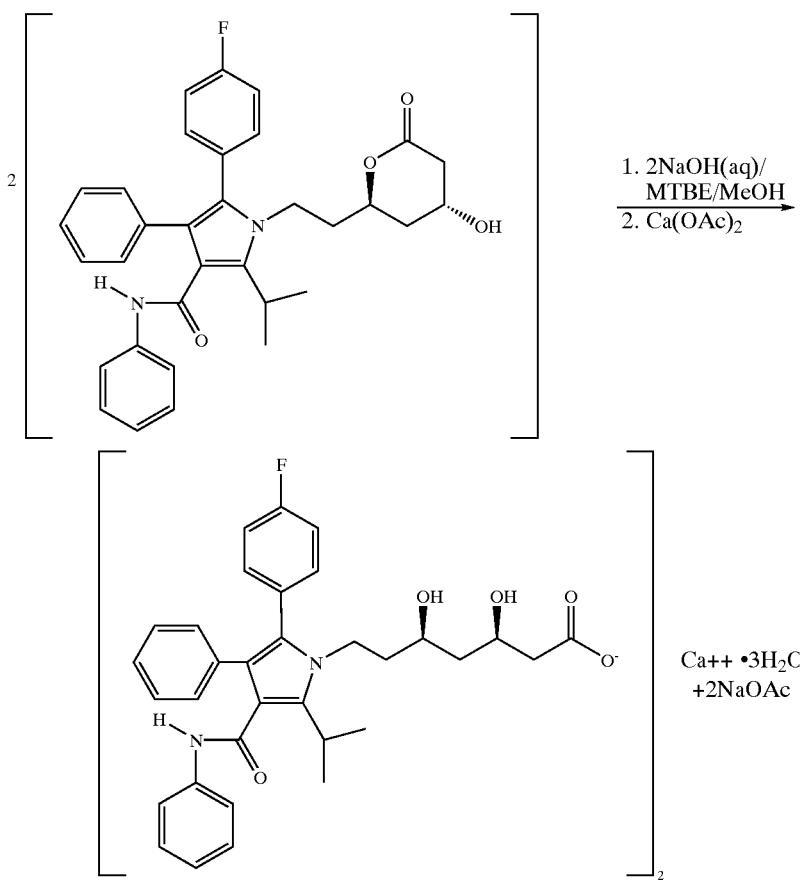

Primarily the crystallization matrix consists of water, some methanol, methyl tert-butyl ether, and sodium atorvastatin.

Methyl tert-butyl ether is an organic compound which is liquid at room temperature. It is used in the process for preparing atorvastatin to remove process-generated impurities and/or impurities present in the lactone.

Methyl tert-butyl ether is very volatile and in the crystallization matrix could be lost to the headspace of the reaction vessel thereby disturbing the equilibrium of the crystallization matrix.

It was found that the addition of an extra charge of methyl tert-butyl ether after extractions with methyl tert-butyl ether ensures a saturated crystallization matrix at the elevated temperature, which has sufficient organic solvent content compensating for any loss to the headspace or increase in solubility with heat, and was surprisingly found to result in the formation of crystals of atorvastatin calcium within a consistent size range on a factory scale.

The invention also provides a process which allows a seed slurry of atorvastatin to be prepared quickly and efficiently and which can be introduced to the reaction vessel under pressure, thereby maintaining a sealed system. A sealed system is maintained throughout the atorvastatin calcium crystallization process to prevent the loss of solvents to evaporation.

Figure 1:
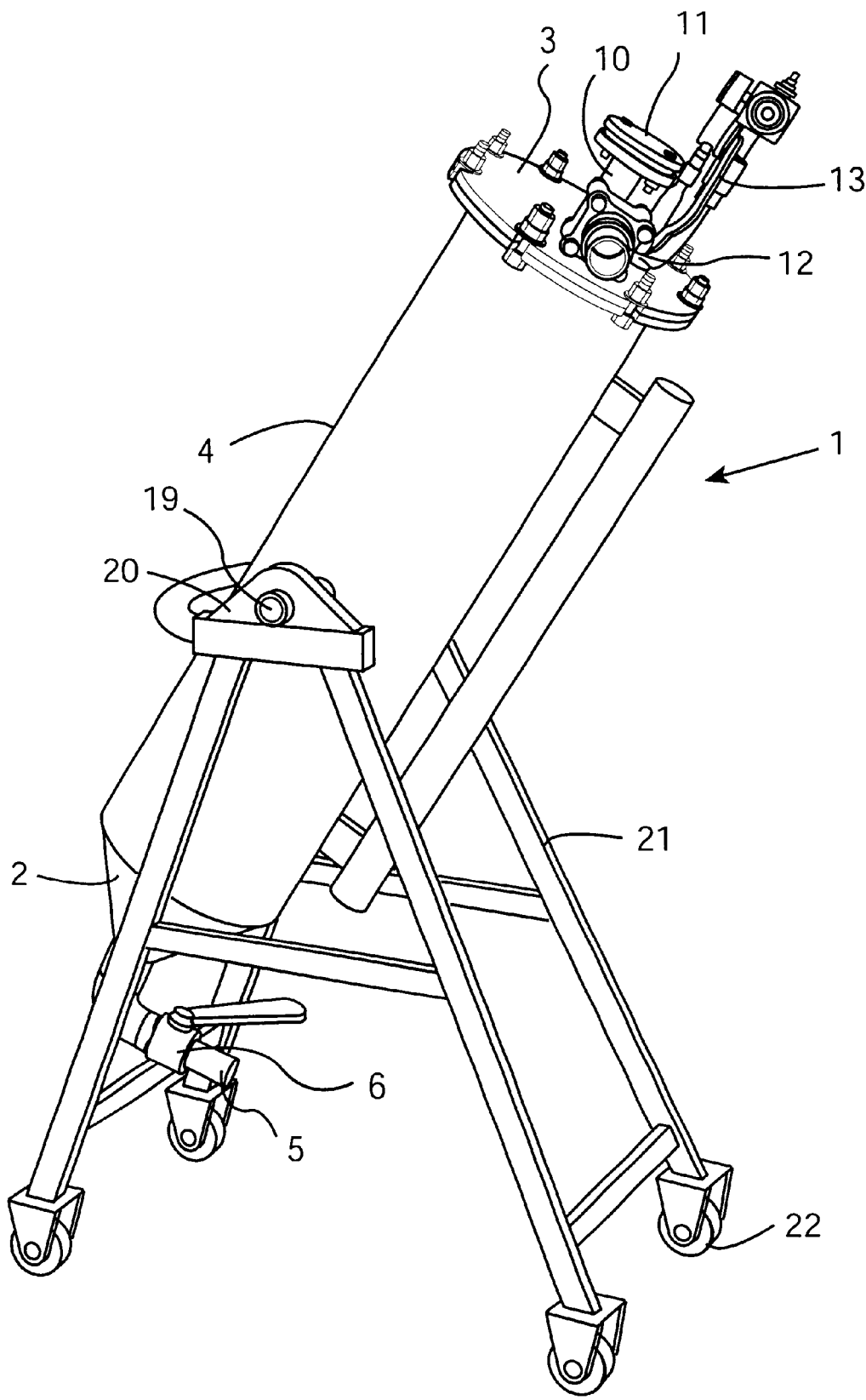
FIG. 1 is a perspective view of a make-up, delivery vessel used in the process of the invention.
Figure 2:
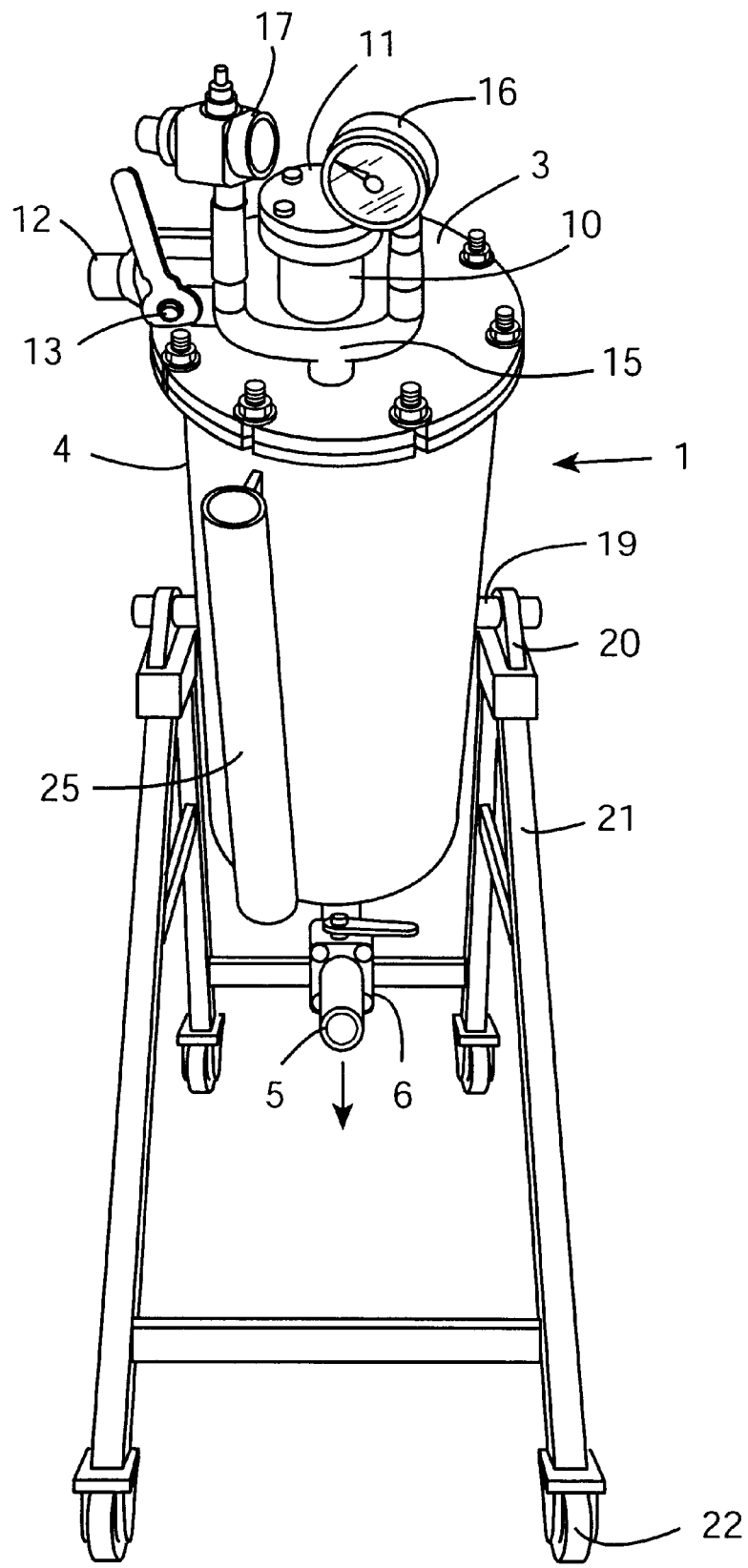
FIG. 2 is a front elevational view of the make-up, delivery vessel.
Figure 3:
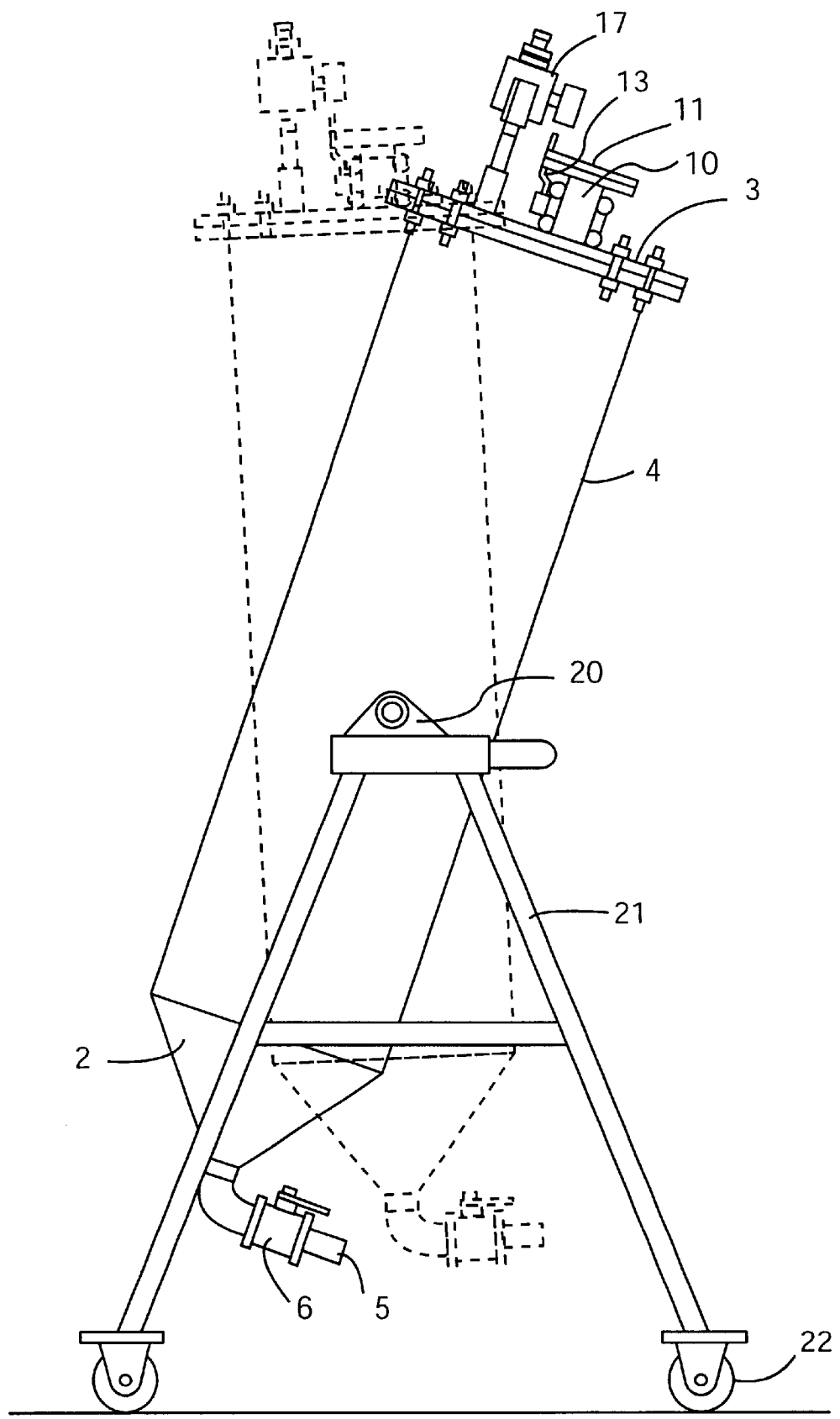
FIG. 3 is a side view of the make-up, delivery vessel illustrating the direction of movement when the vessel is rocked.

FIGS. 1 to 3 illustrate a make-up/delivery vessel 1 to charge, under pressure, atorvastatin calcium seed crystals to a reaction vessel. The make-up/delivery vessel 1 comprises a funneled base 2, a top lid 3, and a generally cylindrical side wall 4 extending between the base 2 and the lid 3. The base 2 has an outlet pipe 5 fitted with a manually operated valve 6. An outlet hose may be connected via a quick release coupling to the outlet pipe 5.

The lid 3 has an inlet pipe 10 with a flanged end 11 and a side branch 12 fitted with a manual valve 13 for connection via a quick-release coupling to a feed hose. The lid 3 has a connecting line 15 with a pressure gauge 16 and a pressure relief valve 17.

A pair of diametrically opposed pins 19 are mounted to and extend outwardly of the side wall 4 to engage in mountings 20 carried on a support frame 21 having ground engaging castors 22. A handle 25 in the form of a length of pipe is attached to the vessel sidewall 4 to facilitate rocking motion of the vessel 1 to mix the contents. In use, solvents are added through the inlet pipe 10 and atorvastatin calcium seed is added after removal of lid 3. Thorough mixing is facilitated by rocking the vessel 1. This process is carried out under pressure and, on completion of mixing, the contents of the vessel 1 are rapidly delivered under pressure through the outlet line 5 to a reaction vessel.

The invention will be more clearly understood from the following example.

EXAMPLE 1

250 kg atorvastatin lactone, 1028 kg methyl tert-butyl ether and 496 kg of methanol are charged to a 6000 L glass-lined reaction vessel. The lactone is prepared as described in U.S. Pat. No. 5,273,995, the entire contents of which are incorporated by reference. The reaction mixture is agitated and heated to about 30° C. to dissolve the lactone. When the lactone is dissolved, approximately 3200 L of caustic solution is added (19 kg of sodium hydroxide 97.5% dissolved in 3165 L deionized water). The contents of the vessel are heated to 47° C. to 57° C. and agitated for at least 45 minutes.

After cooling to 25° C. to 35° C. under an inert atmosphere, the contents are allowed to settle and the organic layer is discarded. 765 kg methyl tert-butyl ether is charged to the aqueous layer, the contents mixed and allowed to settle. The organic layer is discarded.

63 kg of extra methyl tert-butyl ether is charged to the product rich aqueous layer in the reaction vessel which is then sealed. The contents of the sealed reaction vessel are heated to 47° C. to 57° C. maintaining a pressurized system.

A solution of calcium acetate (40 kg calcium acetate hemihydrate in 1365 L deionized water) is transferred to the pressurised vessel. Shortly after commencement of the calcium acetate addition, the transfer is stopped and atorvastatin trihydrate hemi calcium salt seed, prepared as described in U.S. Pat. No. 5,969,156 which is herein incorporated by reference, is introduced.

A seed slurry is prepared by charging 37 L deionized water and 13 kg methanol to a stainless steel make-up/delivery vessel 1 as described above with reference to FIGS. 1 to 3. The solvent mixture is agitated by rocking the vessel 1 back and forth. 3.6 kg atorvastatin calcium seed crystals are then charged to the solvent mixture. The contents of the delivery vessel 1 are then mixed by rocking until a seed slurry is formed. Pressure is applied to the make-up/delivery vessel 1 so that the pressure in the vessel 1 is greater than that of the reaction vessel to which its contents are to be delivered. The make-up/delivery vessel 1 is then attached to the reaction vessel via a flexible hose attached to the outlet pipe 5, and the seed slurry is charged rapidly over 2 to 3 minutes, under pressure, into the reaction vessel. We have found that for optimum results the seed slurry delivery should be commenced not more than 5 and not less than 3 minutes after the addition of calcium acetate.

After the addition of the seed slurry, the calcium acetate addition is immediately resumed to complete the calcium transfer.

The product cake is washed first with a methanol/water solution followed by a water wash. The product is dried at 60° C. to 70° C. under vacuum for 1 to 4 days to yield atorvastatin calcium. The dried product is then loaded into drums.

We have found that the process facilitates routine production of atorvastatin calcium on a factory scale with a consistent size range.

The invention is not limited to the embodiments hereinbefore described which may be varied in detail.

What is claimed is:

1. A factory scale process for producing crystalline atorvastatin trihydrate hemi calcium salt comprising the steps of:
   (a) reacting a mixture of atorvastatin lactone, methanol and methyl tert-butyl ether with sodium hydroxide to form the ring-opened sodium salt;
   (b) forming a product rich aqueous layer and an organic layer comprising methyl tert-butyl ether containing impurities;
   (c) removing the organic layer comprising methyl tert-butyl ether containing impurities;
   (d) extracting the product rich aqueous layer with methyl tert-butyl ether;
   (e) adding an extra charge of methyl tert-butyl ether to a vessel containing the product rich aqueous layer in an amount of at least 1% w/v of the contents of the vessel;
   (f) sealing the reaction vessel;
   (g) heating the contents of the sealed reaction vessel to 47° C. to 57° C. in the presence of the extra charge of methyl tert-butyl ether which saturates the crystallization matrix on heating; and
   (h) adding calcium acetate hemihydrate to the sealed reaction vessel to form atorvastatin trihydrate hemi calcium salt.

2. A process as claimed in claim 1 comprising the steps of: (1) providing a pressurized slurry make-up/delivery vessel and; (2) preparing a seed mixture in the pressurized slurry make-up/delivery vessel by a process comprising the steps of:
   (a) introducing water into the make-up/delivery vessel;
   (b) introducing methanol into the make-up/delivery vessel;
   (c) subsequently adding seed crystals of atorvastatin trihydrate hemi calcium salt to the make-up/delivery vessel; and
   (d) after the addition of calcium acetate hemihydrate, adding the seed mixture thus formed to the sealed reaction vessel from the pressurized make-up/delivery vessel under pressure to maintain saturation of the crystallization matrix by methyl tert-butyl ether at the elevated temperature in the reaction vessel.

3. A process as claimed in claim 2 comprising agitating the methanol and water in the make-up/delivery vessel to produce a solvent mixture before addition of the seed crystals to the make-up/delivery vessel.

4. A process claimed in claim 2 wherein the make-up/delivery vessel comprises a support frame on which the make-up/delivery vessel is pivotally mounted, and the process comprises agitating the methanol and water mixture by rocking the make-up/delivery vessel to produce the solvent mixture.

5. A process as claimed in claim 2 wherein the make-up/delivery vessel comprises a support frame on which the make-up/delivery vessel is pivotally mounted, and the process comprises agitating the solvent mixture and seed crystals by rocking the make-up/delivery vessel to produce the seed crystal slurry.

6. A process as claimed in claim 2 comprising commencing delivery of the seed slurry from the pressurized make-up/delivery vessel into the sealed pressurized reaction vessel not more than 5 minutes after the commencement of the addition of calcium acetate to ensure crystallization simultaneous with the addition of the calcium acetate.

7. A process as claimed in claim 6 comprising commencing delivery of the seed slurry not less than 3 minutes after the addition of calcium acetate.

* * * * *